United States Patent
Kamata et al.

[11] Patent Number: 5,228,071
[45] Date of Patent: Jul. 13, 1993

[54] CT SYSTEM AND METHOD OF USING THE SAME

[75] Inventors: Shoji Kamata, Hitachi; Shigeru Izumi, Tokyo, both of Japan

[73] Assignee: Hitachi, Ltd., Tokyo, Japan

[21] Appl. No.: 799,206

[22] Filed: Nov. 27, 1991

[30] Foreign Application Priority Data

Nov. 29, 1990 [JP] Japan .................. 2-326077

[51] Int. Cl.⁵ .................................. G01N 23/02
[52] U.S. Cl. ......................... 378/20; 378/8; 378/62
[58] Field of Search .......... 378/4, 8, 10, 20, 62, 378/204, 205, 208, 209, 901

[56] References Cited

U.S. PATENT DOCUMENTS

| | | |
|---|---|---|
| 4,422,177 | 12/1983 | Mastronardi et al. ........... 378/20 |
| 4,600,998 | 7/1986 | Huet ................................ 378/20 |
| 4,989,225 | 1/1991 | Gupta et al. .................... 378/20 |
| 5,023,895 | 6/1991 | McCroskey et al. ........... 378/20 |
| 5,119,408 | 6/1992 | Little et al. ..................... 378/20 |

FOREIGN PATENT DOCUMENTS

56-161039 12/1981 Japan .
57-180944 11/1982 Japan .

OTHER PUBLICATIONS

Takahiro Kanamori et al., "Cross-Sectional Imaging of Large and Dense Materials by High Energy X-ray CT Using Linear Accelerator", *Journal of Nuclear Science and Technology*, 26(9), pp. 826–832, 1989.

"Hitachi X-ray Computed Tomography System" pamphlet (no date).

*Primary Examiner*—David P. Porta
*Attorney, Agent, or Firm*—Antonelli, Terry, Stout & Kraus

[57] ABSTRACT

A CT system for cross-sectional imaging and a method using the same are involved. A second table for fine adjustment of an object is arranged on a conventional first table for the object. The center of gravity of a cross-sectional image of the object imaged in advance is determined, the object is finely moved by means of the second table such that the determined center of gravity coincides with the center or a corner of a mesh used for image formation, and cross-sectional imaging is again carried out. Through this, contrast at the edge of the object can be improved when the object is highly symmetrical as are many industrial products.

17 Claims, 3 Drawing Sheets

FIG. 3A
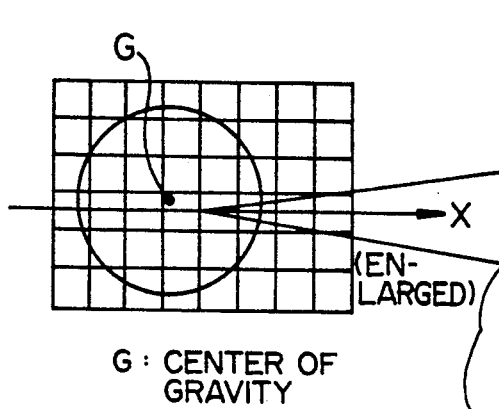
G: CENTER OF GRAVITY
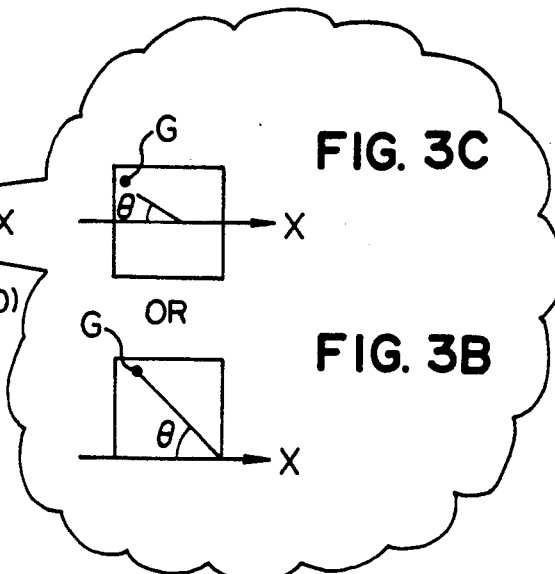
FIG. 3C
OR
FIG. 3B
FIG. 4A
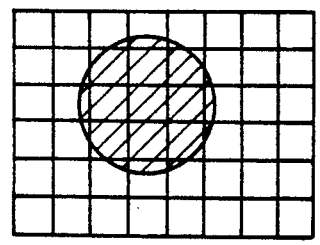
FIG. 4B
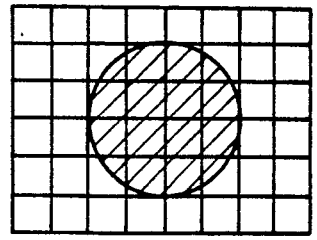

CT SYSTEM AND METHOD OF USING THE SAME

BACKGROUND OF THE INVENTION

The present invention relates to a CT system and a method of using the same and more particularly to a CT system for nondestructive inspection of the inside of industrial products and a method of using the same.

Generally, in this type of CT system, a radiation unit for radiating a radioactive beam and a detector for detecting the radioactive beam are mounted fixedly. An object is carried on a turntable disposed between the radiation unit and the detector and the incident angle of the radioactive beam upon the object is changed by rotating the turntable. The detector detects the radioactive beam transmitted through the object to deliver a detection signal indicative of the intensity of the transmitted radioactive beam. A computer then processes the detection signal to form (reconstruct) a cross-sectional image on a CRT.

For the above technology, reference should be made to a pamphlet "Hitachi X-RAY COMPUTED TOMOGRAPHY SYSTEM" or Journal of Nuclear Science and Technology, 26 [9], pp. 826–832, 1989.

In this type of CT system, in order to obtain high resolution, sensitivity of the detector has to be improved and besides the slit of a collimator interposed between the detector and the object needs to be narrowed. A technique aiming at this approach is disclosed in, for example, JP-A-56-161039 and JP-A-57-180944.

In the former literature, a plurality of detectors are arranged in a fan configuration and the slit width of a collimator associated with a detector in the central region is made to be narrower than that of collimators associated with detectors on both sides, so that radioactive beam transmission data of a central region of an object can be absorbed more finely to provide a cross-sectional image of high resolution.

The latter literature discloses a radioactive source collimator in which between a radioactive source and an object, a disc-shaped element is interposed which is formed, at different portions thereof, with a plurality of kinds of slits having different slit widths, whereby a different slit width can be selected by rotating the disc. In this technique, the radioactive source collimator is normally rotated to use a large-width slit for low resolution/high-speed measurement but when a cross-sectional image of high resolution is needed even at the cost of measurement time, a small-width slit of the collimator is selected by rotating the disc to restrict the radioactive beam, thereby increasing resolution of the cross-sectional image.

Formation of the collimator having a small-width slit as in the above technique is, however time-consuming, raising the production cost of the system.

SUMMARY OF THE INVENTION

An object of the invention is to provide a CT system capable of providing high resolution without narrowing the slit width and a method using the same.

Another object of the invention is to provide a CT system capable of forming a cross-sectional image with high geometrical dimensional accuracy.

To accomplish the above objects, according to the invention, a second unit is interposed between a turntable and an object to permit fine movement of the object. More specifically, the object is finely moved in a direction parallel to a cross-sectional plane to be imaged to make the edge of the cross-sectional image coincident with sides of meshes used for image formation. In this manner, contrast of a resulting image can be improved to thereby improve resolution.

For making the edge of the cross-sectional image coincident with the sides of meshes, in accordance with the invention, cross-sectional imaging is first carried out in the well-known manner and the center of gravity of a resulting cross-sectional image is determined. Then the object is moved such that the center of gravity is brought into coincident with the center of a mesh or a corner of a mesh. Subsequently, cross-sectional imaging is again conducted. Even though the above operation, the edge of a cross-sectional image may not sometimes be completely coincident with the sides of meshes depending on the shape of the cross-sectional image. Even in such an event, by making the center of gravity of the cross-sectional image imaged in advance coincident with the center or corner of a mesh, the edge of the cross-sectional image can be brought into coincidence with sides of meshes with a high probability, thereby making it possible to provide a sharper image than that obtained conventionally.

The edge of the cross-sectional image can also be brought into coincident with the sides of meshes by finely moving the object manually.

Further, in order to observe the shape of a portion such as a cavity, a hole, and/or a crack in an object with a high accuracy, it is desirable that the edge of the portion to be observed be brought into coincidence with the sides of meshes. In this case, it was verified that the portion to be observed could also be observed with a high accuracy by determining the center of gravity of the portion and by moving the object such that the center of gravity of the portion is coincident with the center or a corner of a mesh. This is because the edge of a cross-sectional image can be coincident with the sides of meshes at a higher rate to provide a sharper image than the image obtained conventionally In accordance with the invention, imaging is repeated while an object is finely moved in one direction and resulting cross-sectional images are synthesized or averaged. In this manner, variations in a CT value can be decreased over a series of meshes in which the edge of a cross-sectional image is contained. In other words, by overlapping images with each other, errors in image can be cancelled out, thus ensuring that geometrical dimension of the cross-sectional plane can be measured with high accuracy. Preferably, for measurement of the dimension, the object is imaged together with a reference of a known size.

BRIEF DESCRIPTION OF THE DRAWINGS

FIGS. 3A to 3C are diagrams showing the manner of moving the center of gravity of a cross-sectional image imaged in advance;

FIG. 4A is a diagram showing the relation between the cross-sectional image imaged in advance and individual meshes;

FIG. 4B is a diagram showing a state in which the center of gravity is coincident with a corner of a mesh;

DESCRIPTION OF THE PREFERRED EMBODIMENTS

Preferred embodiments of the invention will now be described with reference to the accompanying drawings.

Figure 1:
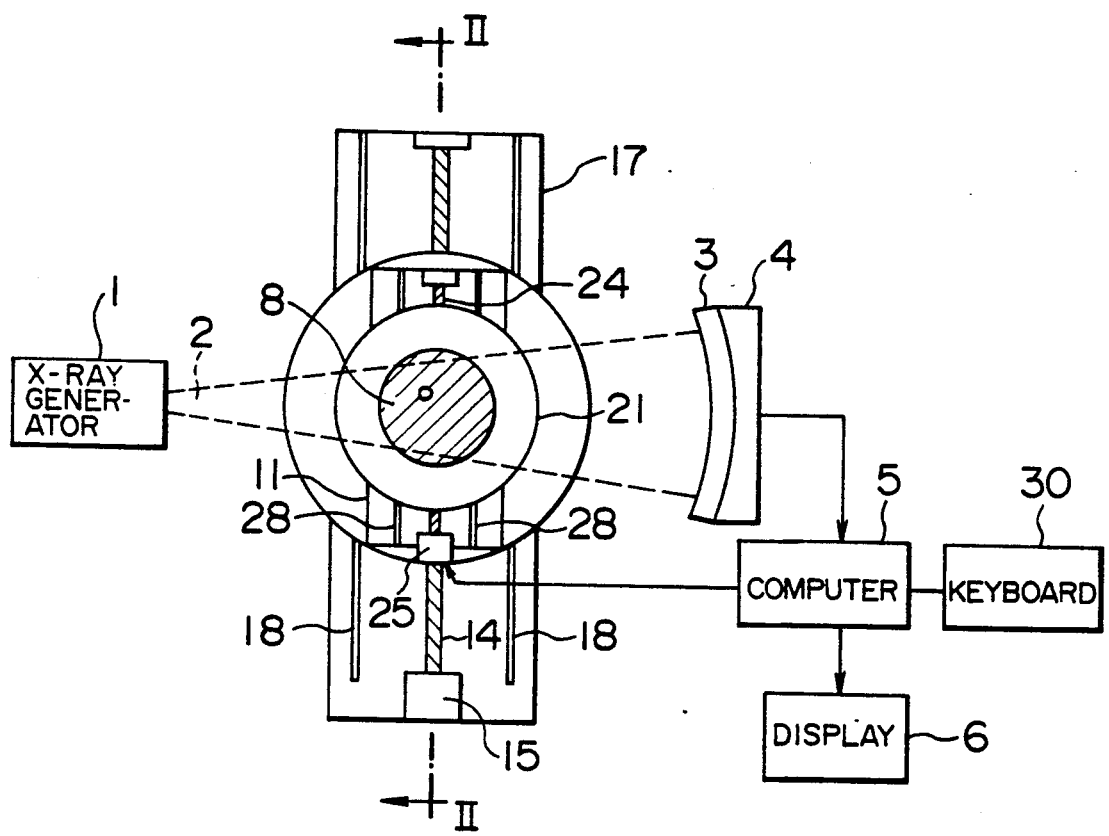
FIG. 1 is a diagram schematically showing an embodiment of a CT system according to the invention.
Figure 2:
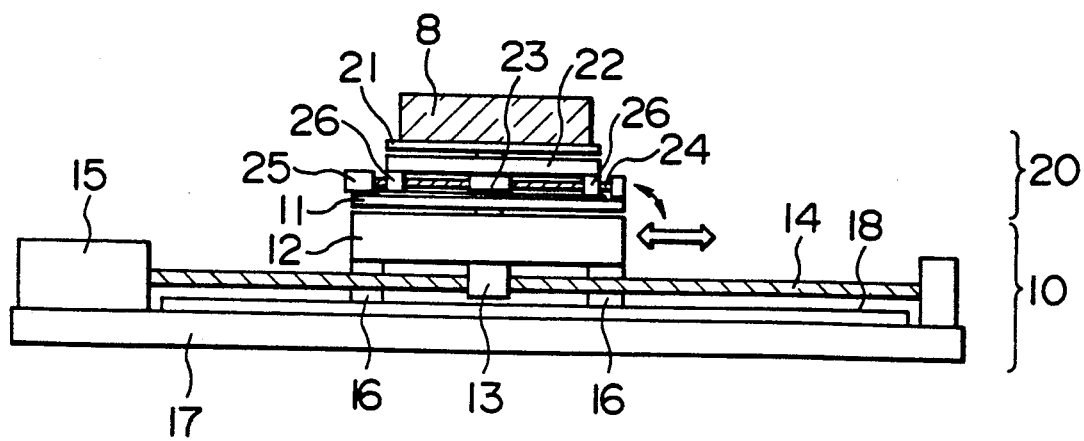
FIG. 2 is a sectional view taken on the line II—II of FIG. 1.

Referring to FIGS. 1 and 2, a CT system according to an embodiment of the invention comprises an X-ray generator 1, a CT scanner 10, an object moving unit 20, a collimator 3, a multi-channel detector (hereinafter referred to as a "detector") 4 and a data acquisition computer (hereinafter referred to as a "computer") 5 and a display 6.

A fan beam 2 of X-rays radiated from the X-ray generator 1 irradiates an object 8. The X-ray beam 2 constitutes a radioactive beam and passes through the collimator 3 to impinge upon the detector 4, so that a signal proportional to an incident intensity value is sent to the computer 5. The computer 5 then acquires data and carries out an image reconstruction operation t provide a cross-sectional image which in turn is displayed on the display 6.

The CT scanner 10 serving as first position changing means includes a first turntable 11 and a scanning bed 12. The turntable 11 is operative to change the incident angle of X-ray beam 2 upon the object 8 and can be rotated intermittently by means of a motor, not shown, mounted to the bed 12. Mounted to the bottom of the bed 12 is a female screw 13 which meshes with a male screw 14. A ball thread was used as the female screw 13. The male screw 14 is driven by a motor 15. The bottom of the bed 12 is also mounted with rollers 16 which roll on a pair of rails 18 laid on a base 17 in parallel with the male screw 14.

The CT scanner 10 is operated synchronously with the x-ray generator 1 and detector 4 under the direction of a control circuit not shown.

The object moving unit 20 serving as second position changing means includes a second turntable 21 and a second bed 22. The second turntable 21 supports on its top surface the object 8 and can be rotated by means of a motor, not shown, mounted to the scanning bed 12. Mounted to the bottom of the second bed 22 is a female screw 23 which meshes with a male screw 24. The male screw 24 is driven by a motor 25. The bottom of the second bed 22 is also mounted with rollers 26 which roll on rails 28 laid on the top surface of the first turntable 11. The male screw 24 and rails 28 are disposed in substantially parallel relationship with the male screw 14 of the CT scanner.

The CT system shown in FIGS. 1 and 2 is used with a short columnar object 8 to obtain a cross-sectional image as shown in FIG. 4A. In the present embodiment, by using the computer 5, the center of gravity G of the object 8 is determined in the cross-sectional image as shown in FIG. 3A, the distance between the corner of a mesh containing the center of gravity G and the center of gravity is determined and the angle $\theta$ between X axis and a line connecting the center of gravity G and the mesh corner is determined (FIG. 3B). Thereafter, the object 8 is rotated by $\theta$ by means of the second turntable 21 and then the second bed 22 is moved to make the center of gravity G coincident with the corner of a mesh. Such movement of the moving unit 20 is effected under the control of the computer 5. Subsequently, cross-sectional imaging is carried out to obtain an image as shown in FIG. 4B. In FIG. 4A, the edge of the cross-sectional image, or the edge of the level of the CT value irregularly spreads over many meshes and consequently blurs, but in FIG. 4B, the edge of the object is coincident with sides of meshes to provide a sharp cross-sectional image which is less blurred.

In the foregoing example, the cross-sectional image has a diameter which is exactly four times one side of a mesh, and therefore when the center of gravity is coincident with a corner of a mesh, the edge of the cross-sectional image can be tangential to sides of meshes. On the other hand, if the diameter of a cross-sectional image is an odd multiple of one side of a mesh, the center of gravity G is brought into coincidence with the center of a mesh as shown in FIG. 3C.

If the diameter of a cross-sectional image is not an integer multiple of one side of a mesh, the edge of the cross-sectional image cannot be coincident with the sides of meshes even when the center of gravity G is moved as shown in FIGS. 3B and 3C. However, since in this case the area occupied by the cross-sectional image is minimized, the number of meshes over which the edge of the cross-sectional image spreads irregularly can be reduced to make the edge of the cross-sectional image smooth and sharp.

In the foregoing embodiment, the center of gravity of the object 8 is finely moved through rotation and linear movement, but it can of course be moved through linear movements in two directions. Typically, the two movement directions are set to lie in directions of two adjacent sides of a mesh. In other words, the object may be moved in a desired direction parallel to a cross-sectional plane.

In accordance with the present embodiment, the resolution can advantageously be improved to a value of theoretical spatial resolution prescribed by the mesh.

Figure 6:
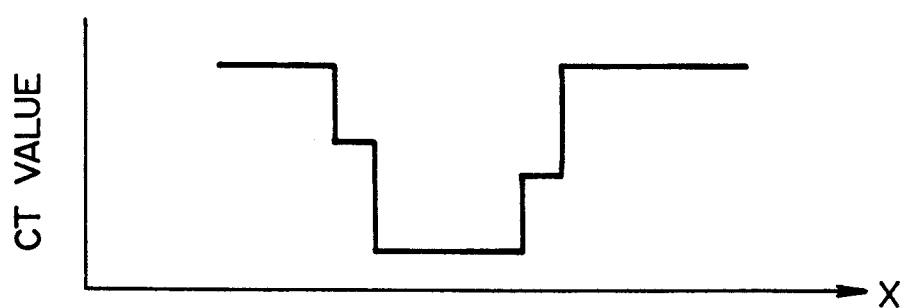
FIG. 6 is a graphical representation showing CT values the X axis of FIG. 5.
Figure 7:
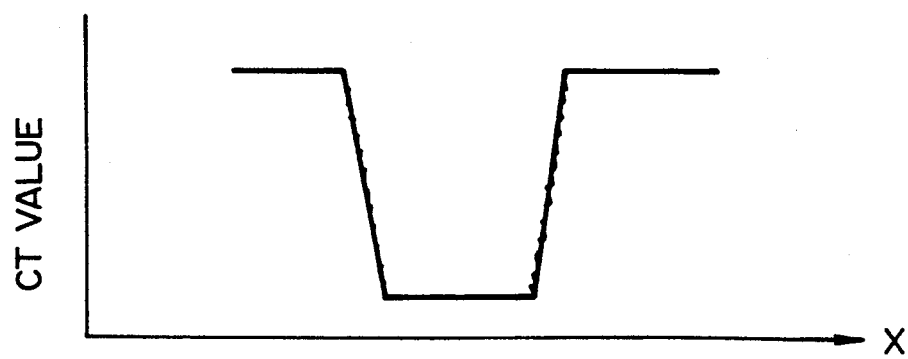
FIG. 7 is a graphical representation showing CT values on the X axis obtained when imaging is repeated while the object is moved finely to form a cross-sectional image similar to that of FIG. 5.

Another embodiment will be described with reference to FIGS. 5 to 7.

Figure 5:
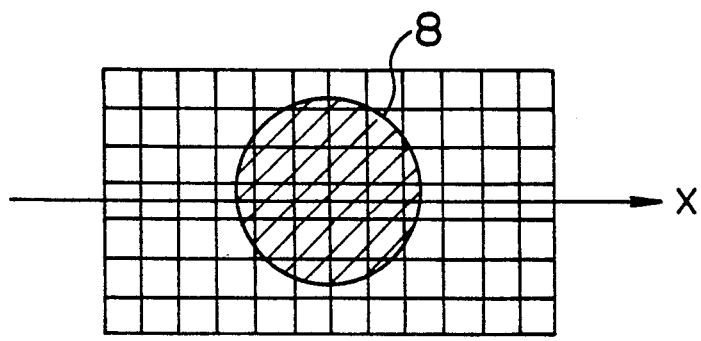
FIG. 5 is a diagram showing an example of a cross-sectional image.

FIG. 5 shows a result of cross-sectional imaging of an object 8. In FIG. 5, a region surrounded by four straight lines of which two adjacent vertical and lateral lines cross with each other at right angles corresponds to one mesh. CT values of meshes measured on the X axis of FIG. 5 are shown in FIG. 6.

Ideally, the CT value should be 1 (one) at a portion where the object is present and 0 (zero) at a portion outside the object where air is present. Practically, however, under the influence of scattered rays from the object 8 and the influence of a lack of a high-band component in the filter function used for image reconstruction, the CT value changes stepwise at the edge of the object 8 as shown in FIG. 6. When imaging is effected under the condition that the edge of the object 8 is not coincident with sides of meshes, the CT value changes to take a step form having different right and left contours as shown in FIG. 6, in contrast to the CT value which should essentially change by keeping right-left symmetry maintained. In such an event, the form of the cross-sectional image changes depending on a set level of a threshold. In other words, the cross-sectional image cannot accurately represent the form of the object, thereby degrading the spatial resolution.

To cope with this problem, in accordance with the invention, the object 8 is translated by a fraction of a side of a mesh by means of the second bed 22. For example, cross-sectional imaging is carried out while an object 8 is moved by 1/10 of the side of a mesh by means of the bed 22 and subsequently cross-sectional imaging is done while the object 8 is further moved by 1/10 of the side of a mesh in the same direction as in the preceding step. The above operation is repeated nine times to provide nine cross-sectional images Changes in the CT value on the X axis of FIG. 5 of these nine cross-sectional images are overlapped with each other on one sheet to provide a form as shown in FIG. 7. The number of meshes on the X axis is equivalently increased to 10 times the number in FIG. 6, and changes in the CT value are smoothed.

Cross-sectional imaging is effected while an object 8 is finely moved together with a reference of a geometrical dimension which is known in advance by means of the second bed 22. When the threshold level of the CT value is so set that the CT value of a resulting cross-sectional image accurately represents the known dimension of the reference, accuracy of dimensional measurement can be improved in connection with a cross-sectional image of the object 8 to 1/10 of the side of a mesh as compared to cross-sectional imaging effected under the movement mesh by mesh.

Setting of the threshold level is carried out manually using a keyboard 30 in FIG. 1. This keyboard 30 is also used to manually operate the movement of the second bed 22 as well as the second table 21.

Although the present invention has been described in detail, it should be understood that various changes, substitutions and alternations can be made hereto without departing from the spirit and scope of the present invention as defined by the appended claims.

We claim:

1. A system for cross-sectional imaging of an object comprising:
    radiation means for irradiating an object with a radioactive beam such that the radioactive beam passes through said object;
    first position changing means for changing an angle at which the radioactive beam is incident to said object in an imaginary plane containing a cross-sectional plane of said object to be imaged;
    detection means for detecting the radioactive beam after the radioactive beam has passed through said object and outputting a detection signal indicative of the detected radioactive beam;
    means for forming a cross-sectional image of the cross-sectional plane of said object on a plurality of meshes by processing said detection signal;
    second position changing means for finely moving said object substantially parallel to said cross-sectional plane of said object to be imaged; and
    control means for determining a center of gravity of said cross-sectional image and controlling said second position changing means based on the center of gravity of said cross-sectional image.

2. A cross-sectional imaging system according to claim 1, wherein said control means controls said second position changing means based on the center of gravity of said cross-sectional image to finely move said object such that the center of gravity of said cross-sectional image coincides with a corner of one of the meshes.

3. A cross-sectional imaging system according to claim 1, wherein said control means controls said second position changing means based on the center of gravity of said cross-sectional image to finely move said object such that the center of gravity of said cross-sectional image coincides with a center of one of the meshes.

4. A cross-sectional imaging system according to claim 1, wherein said second position changing means is disposed on said first position changing means and is operable independently of said first position changing means.

5. A cross-sectional imaging system according to claim 1, wherein said radioactive beam is an X-ray beam.

6. A cross-sectional imaging system according to claim 1, wherein said radiation means and said detection means are stationary, and wherein said first position changing means includes means for rotating the object about an axis extending in a direction substantially orthogonal to a direction in which said radiation means irradiates said object with said radioactive beam.

7. A cross-sectional imaging system according to claim 6, wherein said first position changing means includes means for moving said object substantially parallel to said cross-sectional plane of said object to be imaged and substantially orthogonal to a direction in which said radiation means irradiates said object with said radioactive beam.

8. A cross-sectional imaging system according to claim 1, wherein said cross-sectional image forming means includes a display for displaying said cross-sectional image.

9. A cross-sectional imaging system according to claim 2, wherein said control means also controls said second position changing means based on a size of the meshes.

10. A system for cross-sectional imaging of objects comprising:
    radiation means for irradiating a beam of radioactive rays on an object;
    first position changing means for changing the incident angle of the radioactive beam upon said object in an imaginary plane containing a cross-sectional plane to be imaged of said object;
    detection means for detecting a radioactive beam transmitting through said object and delivering a detection signal in accordance with the transmitting radioactive beam;
    means for forming a cross-sectional image of said object by processing said detection signal; wherein the image is reconstructed on meshes;
    second position changing means for finely moving said object in substantially parallel relationship with said cross-sectional plane to be imaged; and
    control means for determining the center of gravity of said cross-sectional image and controlling said second position changing means by utilizing the determined center of gravity;
    wherein said control means controls said second position changing means such that the center of gravity of said cross-sectional image coincides with a corner of a mesh.

11. A method for cross-sectional imaging of an object, comprising the steps of:
    irradiating an object with a radioactive beam such that the radioactive beam passes through said object;
    changing an angle at which said radioactive beam is incident to said object in an imaginary plane containing a cross-sectional plane of said object to be imaged;

detecting the radioactive beam after the radioactive beam has passed through said object and outputting a detection signal indicative of the detected radioactive beam;

forming a cross-sectional image of said object on a plurality of meshes by processing said detection signal;

determining a center of gravity of said cross-sectional image; and finely moving said object substantially parallel to said cross-sectional plane of said object to be imaged based on the center of gravity of said cross-sectional image.

12. A system for cross-sectional imaging of objects comprising:

radiation means for irradiating a beam of radioactive rays on an object;

first position changing means for changing the incident angle of the radioactive beam upon said object in an imaginary plane containing a cross-sectional plane to be imaged of said object;

detection means for detecting a radioactive beam transmitting through said object and delivering a detection signal in accordance with the transmitting radioactive beam;

means for forming a cross-sectional image of said object by processing said detection signal; wherein the image is reconstructed on meshes;

second position changing means for finely moving said object in substantially parallel relationship with said cross-sectional plane to be imaged; and control means for determining the center of gravity of said cross-sectional image and controlling said second position changing means by utilizing the determined center of gravity;

wherein said control means controls said second position changing means such that the center of gravity of said cross-sectional image coincides with a corner of a mesh.

13. A system for cross-sectional imaging of an object comprising:

radiation means for irradiating an object with a radioactive beam such that the radioactive beam passes through said object;

first position changing means for changing an angle at which the radioactive beam is incident to said object in an imaginary plane containing a cross-sectional plane of said object to be imaged;

detection means for detecting the radioactive beam after the radioactive beam has passed through said object and outputting a detection signal indicative of the detected radioactive beam;

means for forming a cross-sectional image of the cross-sectional plane of said object on a plurality of meshes by processing said detection signal;

second position changing means for finely moving said object substantially parallel to said cross-sectional plane of said object to be imaged; and control means for controlling said second position changing means to finely move said object to a plurality of imaging positions equally spaced along a line having a length equal to a length of one side of one of the meshes;

wherein said cross-sectional image forming means forms the cross-sectional image by synthesizing a plurality of cross-sectional images respectively formed at the plurality of imaging positions.

14. A cross-sectional imaging system according to claim 13, wherein the cross-sectional image forming means also forms a reference cross-sectional image having a known geometrical dimension, and further comprising means for setting a threshold level based on the known geometrical dimension of the reference cross-sectional image, wherein the cross-sectional image forming means forms said cross-sectional image by processing said detection signal based on the threshold level.

15. A system for cross-sectional imaging of an object comprising:

radiation means for irradiating an object with a radioactive beam such that the radioactive beam passes through said object;

first position changing means for changing an angle at which the radioactive beam is incident to said object in an imaginary plane containing a cross-sectional plane of said object to be imaged;

detection means for detecting the radioactive beam after the radioactive beam has passed through said object and outputting a detection signal indicative of the detected radioactive beam;

means for forming a cross-sectional image of the cross-sectional plane of said object on a plurality of meshes by processing said detection signal;

second position changing means for moving said object substantially parallel to said cross-sectional plane of said object to be imaged; and control means for controlling said second position changing means to move said object such that an edge of said cross-sectional image coincides with a side of one of the meshes.

16. A cross-sectional imaging system according to claim 15, wherein the control means includes:

means for determining a center of gravity of said cross-sectional image; and means for controlling said second position changing means based on the center of gravity of said cross-sectional image to move said object such that the center of gravity of said cross-sectional image coincides with a corner of one of the meshes, thereby causing an edge of said cross-sectional image to coincide with a side of one of the meshes.

17. A cross-sectional imaging system according to claim 15, wherein said control means includes:

means for determining a center of gravity of said cross-sectional image; and means for controlling said second position changing means based on the center of gravity of said cross-sectional image to move said object such that the center of gravity of said cross-sectional image coincides with a corner of one of the meshes, thereby causing an edge of said cross-sectional image to coincide with a side of one of the meshes.

* * * * *